United States Patent [19]

Oosterhoff

[11] Patent Number: 5,580,940
[45] Date of Patent: Dec. 3, 1996

[54] BIODEGRADABLE DIACRYLATES AND ADHESIVES BASED THEREON

[75] Inventor: Rudolf H. Oosterhoff, Ede, Netherlands

[73] Assignee: Lions Adhesives, Inc., Lansing, Mich.

[21] Appl. No.: 420,956

[22] Filed: Apr. 12, 1995

[51] Int. Cl.$^6$ .......................... C07H 13/12; C08F 20/36; C08F 20/58; C09J 4/02
[52] U.S. Cl. ...................... 526/238.23; 536/17.9
[58] Field of Search ...................... 536/17.9; 526/238.23

[56] References Cited

U.S. PATENT DOCUMENTS

| | | | |
|---|---|---|---|
| 3,297,745 | 1/1967 | Fekete et al. | 526/301 |
| 3,907,865 | 9/1975 | Miyata et al. | 260/471 C |
| 4,833,202 | 5/1989 | Dunn, Jr. | 525/54.2 |

FOREIGN PATENT DOCUMENTS

| | | |
|---|---|---|
| 9201695 | 4/1994 | Netherlands . |
| 862567 | 1/1983 | U.S.S.R. . |
| 1193601 | 6/1970 | United Kingdom . |

OTHER PUBLICATIONS

*Chemical Abstracts,* vol. 101, 1984, Columbus, Ohio, U.S., R. Pernikis et al., "Derivatives of 1,6–anhydro–β–d–glucopyranose for three–dimensional polymerization."

*Primary Examiner*—Frederick Krass
*Attorney, Agent, or Firm*—Quarles & Brady

[57] ABSTRACT

Biodegradable diacrylates containing both a polymerizable double bond and a mono- or disaccharide residue are useful in the preparation of biodegradable polymers which can be used as adhesives. Methods of making the diacrylates and polymers are disclosed.

20 Claims, No Drawings

BIODEGRADABLE DIACRYLATES AND ADHESIVES BASED THEREON

FIELD OF THE INVENTION

The present invention generally relates to polymers. More particularly, the invention pertains to di(meth)acrylate monomers and the prepolymers and polymers prepared therefrom which are useful as biologically degradable adhesives.

BACKGROUND OF THE INVENTION

An increasingly important requirement of adhesives is that they not only have good adhesive properties, but that they are also biodegradable. The common adhesives, however, do not meet this requirement and strong adhesives are generally not at all biodegradable, or only to a small extent.

A number of biodegradable pollers are know including poly(lactic acid), poly(glycolic acid), poly(hydroxybutyrate) and the like. These pollers are degradable in aqueous environments. They are used for medical applications, such as implants, medicine and surgical materials. However, they are not suitable for adhesives or glues. At best they can serve as binders in aqueous solutions for certain applications.

Mixtures of natural pollers and synthetic pollers are known which can be used as biodegradable compositions, such as starch in combination with nylon, polyropylene, or polystyrene. Also known are combinations of gelatin and resorcinol-formaldehyde resin, which are biodegradable.

In addition, pollers are known which in aqueous solution can serve as adhesives and which are biodegradable as well. Examples of these are poly(vinyl alcohol), poly(ethylene oxide), poly(vinyl pyrrolidone) and the like. These pollers can, however, only be used in aqueous environment and have only a limited range of applications. Also known are derivatives of natural products which are biodegradable and have adhesive properties, such as carboxymethyl cellulose, amylose from starch, and casein from milk.

Biodegradable adhesives made from these known products either have adhesive properties which are insufficient or applications which are limited.

BRIEF SUMMARY OF THE INVENTION

The objects of the present invention are to disclose new biodegradable adhesives, novel starting materials for making such adhesives and novel methods of making such adhesives.

I have discovered a group of monomers which are suitable as a basis for biodegradable adhesives, with good adhesive properties.

The monomers according to this invention are in particular di(meth)acrylate monomers corresponding to the following formula:

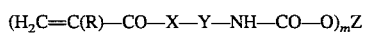

$(H_2C=C(R)-CO-X-Y-NH-CO-O)_m Z$    1 in which: R represents a hydrogen atom or a lower alkyl group of 1 to 4 carbon atoms, preferably a methyl group; X represents a direct bond, an oxygen atom or imino group; Y is a direct bond, or a $C_{1-22}$-hydrocarbon group, optionally substituted with one or more hydroxyl groups and/or interrupted by one or more ether, ketone, ester, amide, carbonate, urethane, or urea moieties; Z represents a mono- or disaccharide moiety; and m is an integer with an average value between 1.9 and 3.

The monomers of the present invention contain both a polymerizable double bond, and a mono- or disaccharide residue. In addition to the monomers of formula 1, monomers containing for example a styrene or butadiene unit are also suitable, such as bis[N-(α,α-dimethyl-m-isopropentyl-benzyl) carbamyl]-monosaccharides, in which the CO—X group in formula 1 has been substituted by an aryl group. In addition to the urethanes of formula 1, acrylates without the urethane functionality are suitable, such as bis[3-(meth)acryloyl-oxy-2-hydroxypropyl]-monosaccharides, which are obtainable for example by the reaction of glycidyl-(meth)acrylate with a monosaccharide.

The monomer of the present invention consists therefore of a mono- or disaccharide functionality, such as glucose or sucrose, to which, preferably via a urethane linkage, an acrylate functionality or other polymerizable group is connected. The combination of an acrylate-and/or urethane functionality and a mono- or disaccharide, leads to adhesives having strong adhesion to many materials. Owing to the acrylate functionality, rapid hardening (or setting) is possible. The flexibility of the urethane linkage ensures that the molecule can orient itself to the adhering surface.

Where the word "acrylate" is used herein, acrylate analogs, such as α- or β-substituted acrylates, including alkyl, alkenyl, cyano, carbamyl, carboxyl, alkoxycarbonyl or halogen-substituted acrylates, and particularly methacrylate, are also included.

Because of the mono- or disaccharide moieties, the monomers of the present invention and the oligomers and polymers derived therefrom, are susceptible to biodegradation. "Biodegradation" as used herein is understood to mean the property of being dissected to small unharmful units under environmental conditions under the influence of microorganisms, plants or by enzymes supplied via other means.

The residue denoted by the symbol Z in Formula 1 is preferably a monosaccharide residue, in particular a pentose or hexose residue with the molecular formula $C_5H_8O_3$ and $C_6H_{10}O_4$, resp., or a similar polyol residue with the molecular formula $C_5H_{10}O_3$ and $C_6H_{12}O_4$, resp. Examples of these sugars include arabinose, ribose, glucose, fructose, mannose, xylitol, sorbitol and mannitol. The monosaccharides and polyols can optionally be derivatized, such as with acetyl-, hydroxyl- and amino groups. In particular, the monosaccharide residue is derived from glucose. Preferably, to each mono- or disaccharide two side chains—O—CO—NH—Y—X—CO—C(R)=CH$_2$ are attached, i.e. m=2; in a mixture of saccharide-di(meth)acrylates with formula 1, m can be larger than 2 for a small number of saccharides, for example 3 or 4. Generally, the average value of m is between 1.9 and 3, particularly in between 2 and 2.2. It is noted that for the case of m≠2, the number of oxygen and hydrogen atoms in the above molecular formulas of the mono- or disaccharide residues are inversely smaller or larger.

Examples of acrylates of formula 1 are bis(meth)acryloyl-carbamyl) glucose (in which X—Y is a direct bond) and bis(meth)acryloyloxyethyl-carbamyl) glucose (in which X is oxygen and Y is ethylene).

Especially preferred are monomers having the following formula:

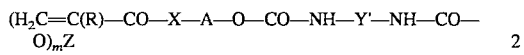

$(H_2C=C(R)-CO-X-A-O-CO-NH-Y'-NH-CO-O)_m Z$    2 in which: A represents a $C_1-C_8$-alkylene group, optionally substituted with one or more hydroxyl groups and/or interrupted by one to three ether functionality's; Y' represents a $C_{2-22}$-hydrocarbon group, optionally interrupted by an ether functionality; and m, R, X and Z are as described for formula 1.

Examples of the group A are ethylene, 1,2-propylene, trimethylene (1,3-propylene), tetramethylene, 2-methylpentamethylene, hexamethylene, 2-hydroxytrimethylene, 1-hydroxymethyl-ethylene, 2,2-bis(hydroxymethyl)trimethylene, 2,3-dihydroxy-tetramethylene, oxydiethylene, oxydipropylene, dioxytriethylene and trioxytetraethylene. Preferably group A is a $C_1$–$C_6$-alkylene-, 2-hydroxy-trimethylene-, or a oxydiethylene group. Depending on the nature of groups R and X, the group A is attached to an acryloyloxy-, methacryloyloxy-, acryamido- or methacrylamido group.

The group Y' can be an unsaturated or saturated hydrocarbon group, which consists of alkylene-, alkenylene-, alkynylene-, cycloalk(en)ylene- and arylene groups and can be substituted with alkyl- and aryl groups. Optionally, the hydrocarbon group is interrupted by ether bonds. Examples of such hydrocarbons are tetramethylene, 2-methylpentamethylene, oxydipropylene, hexamethylene, dodecamethylene, cyclohexylene, methylcyclohexylene, phenylene, biphenylene, toluene, xylylene, naphthalene, methylenediphenylene, oxydiphenylene, etc. A suitable group is 1,5,5-trimethyl-1-methylene-1,3-cyclohexene (isophrone-diyl).

The monomers of formula 1 are sugar-urethane-diacrylates and they can be prepared by the method which comprises reacting an isocyanate of the formula $H_2C{=}C(R)$—CO—X—Y—NCO with a mono- or disaccharide having the general formula $Z(OH)_2$, wherein R, X, Y and Z are as described above. An example of this is the reaction of isocyanate ethyl methacrylate with glucose.

The preferred compounds of formula 2 are sugar-diurethanediacrylates and they can, in addition to the abovementioned method, be prepared from three starting materials:

(I) a hydroxyalkyl-(meth)acrylate or-(meth)acrylamide with the formula $H_2C{=}C(R)$—CO—X—A—OH, (II) a diisocyanate with the formula OCN—Y'—NCO, and (III) a monosaccharide with the formula $Z(OH)_2$.

Examples of starting material (I) are hydroxyethyl acrylate, hydroxyethyl methacrylate, hydroxypropyl methacrylate, 2,3-dihydroxypropyl acrylate, hydroxyhexyl methacrylate, pentaerytrityl methacrylate, N-hydroxymethyl methacrylamide and N,N-bis(hydroxyethyl) acrylamide.

Examples of the starting material (II) are the previously mentioned diisocyanates containing the symbol Y'.

Examples of the starting material (III) are the previously mentioned monosaccharides and polyols containing the group Z.

The starting materials (II) and (III) can first be reacted to form a diisocyanate with the formula (OCN—Y'—NH—CO—O)$_2$Z, which is subsequently converted by reaction with (I) to form the diacrylates of the present invention.

Alternatively, the starting materials (I) and (II) can first be reacted to form an isocyanato-acrylate with the formula $H_2C{=}C(R)$—CO—X—A—O—CO—NH—Y'—NCO, which is subsequently converted by reaction with a monosaccharide (III) to the diacrylates of the present invention.

In another possible synthesis, the starting materials, (I), (II), and (III), can all be reacted at the same time to form the diacrylates.

In the above, A, R, X, Y, Y' and Z are as described previously; although in the above by way of example the ratio of diisocyanate (II) to monosaccharide (III) is 2:1 (i.e. m=2), a part of the reaction can occur with a higher ratio and a small part of the reaction can occur with a lower ratio, provided the average of m in the final product is between 1.9 and 3.

In the method in which first the monosaccharide (III) is treated with the diisocyanate (II), a small molar excess of diisocyanate, for example 2–3 mole, in particular 2–2.5 mole OCN—Y'—NCO per mole of monosaccharide, is added to the monosaccharide. Preferably, this is carried out in an inert solvent, such as an aprotic, polar solvent. Useful examples of such a solvent are dimethylformamide (DMF), N-methylpyrrolidone, dimethylsulfoxide (DMSO), sulfolaan (tetramethylene sulphone), hexamethyl phosphortriamide (HMPA), acrylonitrile, benzonitrile, nitromethane, nitrobenzene, ethers such as diethyl ether, diisopropyl ether, diphenyl ether, anisole, tetrahydrofuran (THF), dioxane, dimethoxy ethane, diethylene glycol dimethyl ether (triglyme), esters such as ethyl acetate, and methoxyethyl acetate, ketones such as methyl ethyl ketone, cyclohexanone, and aromatic hydrocarbons, such as toluene xylene and chlorobenzene. Mixtures of such solvents are also applicable.

The reaction can also be carried out in a monomer as solvent. The advantage of this is that after the reaction the solvent does not need to be completely separated from the product, but can be a part of the (pre)polymer which serves as the base for the adhesive. Examples of useful monomers are mono-, di-, and trihydroxyalkyl acrylates, caprolactone acrylates, vinyl esters such as vinyl acetate, vinyl propionate and vinyl butyrate, and in particular vinyl ethers such as vinyl methyl ether, vinyl ethyl ether, vinyl butyl ether, and di and triethylene glycol divinyl ether.

The reaction between (II) and (III) can be carried out under existing and known urethane-forming conditions, for example at a temperature between room temperature and 100° C., optionally in the presence of a catalyst such as an amine or an ammonium salt. If needed, pressure can be applied, in particular when using a volatile solvent such as a monomer.

The thus obtained intermediate product of the reaction of starting materials (II) and (III) has the formula (OCN—Y'—NH—CO—O)$_2$Z and it is, with or without purification (optional removal of the excess diisocyanate, solvent or catalyst), reacted further with the hydroxyalkyl acrylate (I). The hydroxy compound is added at an approximately stoichiometric amount or in slight excess, in particular at a molar excess of 2 to 3 relative to the intermediate product. For this reaction the same solvents and conditions can be used as described previously for the reaction of (II) and (III).

When, according to a preferred method of this invention, an isocyanato-acrylate with the formula $H_2C{=}C(R)$—CO—X—Y—NCO is reacted as a starting material or as an intermediate product (by reaction with hydroxyacrylate with diisocyanate), with a mono- or disaccharide, the same conditions and solvents can be applied as described above. In the reaction between isocyanate and mono- or disaccharide an approximately stoichiometric amount of saccharide (1.8–2.2:1) is used relative to the isocyanate. In this reaction the use of a monomer as solvent is applicable as mentioned above. When the isocyanate is prepared from hydroxy acrylate and diisocyanate, a small excess of diisocyanate is preferably used in the first step relative to the hydroxy compound (2–2.5:1).

The invention also can be used to prepare polymers by the polymerization of a diacrylate as described above. Such a polymer preferably has the structure of formula 3:

[$H_2C$—$CT(R)$—CO—X—Y—NH—CO—O—Z—O—CO—NH—Y—X—CO—$CT(R)$—$CH_2$]$_n$     3 particularly [$H_2C$—$CT(R)$—CO—X—A—O—CO—NH—Y'—NH—CO—O—Z—O—CO—NH—Y'—NH—CO—O—A—X—CO—$CT(R)$—$CH_2$]$_n$ in which T represents a hydrogen or a chain-ending group; n represents an integer from 2 to 1000, and A, R, X, Y, Y' and Z are as previously described. By a chain-ending group is meant a group which is available in a polymerization medium and can transfer a radical formed during the polymerization. Examples are a hydrogen atom or a hydroxyl group, a solvent residue, and initiator residue such as a lauryl or benzyl group or a group —C(R)(=CH)—CO-etc.

Moreover, the polymer can also contain a double bond at the linkage point of the two acrylate groups and/or be linked to the R-group bound hydrogen atom as for example in the following formula:

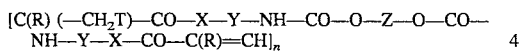
                                                                4

Consequently, the polymers according to the invention are preferably predominantly head-to-tail polymers of the di(meth)acrylate described above, which contain few poly(meth)acrylate chains. The polymers according to the invention also can be copolymers of the di(meth)acrylate described above, with other monomers such as alkyl (meth)acrylates, hydroxyalkyl (meth)acrylates, alkylene di(meth)acrylates, sugardi(meth)acrylates, (meth)acrylonitrile, vinyl esters, styrenes, etc.

The term "polymers" as used herein is to be understood to mean all macromolecular compounds in which at least two di(meth)acrylate units of the present invention are present. Accordingly, prepolymers and oligomers are also included.

The polymers according to the invention can be obtained via existing and known methods of polymerization of the di(meth)acrylates described above. For example, the polymers can be made by polymerization using thermal initiators such as peroxides and hydroperoxides, such as benzoyl peroxide, lauryl peroxide, butyl hydroperoxide, azo compounds such as azoisobutyronitrile, and the like. The polymers can also be obtained via polymerization using photochemical initiators, such as benzophenone, benzoin, (di)sulfides and thiols.

A prepolymer of the present invention can be used exceptionally well as a monomer adhesive. For this use, the prepolymer is used in combination with an organic peroxide or mixed with a photochemical initiator, and used directly as an adhesive for metal, synthetics, ceramic, glass, and other materials. Laminates can also be made of wood, paper or cardboard and the like using the adhesive.

A prepolymer of the present invention can, be conveniently prepared via aqueous emulsion polymerization. A polymeric dispersion can then be formed of the polymer in water. This polymer in water can be used directly as a fast packaging adhesive, a wood glue, a synthetic adhesive and the like. A fast packaging adhesive is one that can be used on high speed packaging equipment.

It will be apparent to those skilled in the art that a number of modifications and changes may be made without departing from the spirit and scope of the invention. Therefore, it is intended that the invention be limited only by the claims.

I claim:

1. A diacrylate having the following formula:

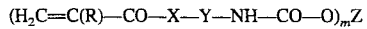                                             1 in which: R represents a member selected from the group consisting of a hydrogen atom and a lower alkyl group of 1 to 4 carbon atoms; X represents a member selected from the group consisting of a direct bond, an oxygen atom and an imino group; Y is a member selected from the group consisting of a direct bond, an alkylene group of 1 to 22 carbon atoms, and an alkylene group of 1 to 22 carbon atoms having at least one member selected from a hydroxyl, an ether, a ketone, an ester, an amide, a carbonate, a urethane, or a urea moiety; Z represents a mono- or disaccharide residue; and m is an integer with an average value between 1.9 and 3.

2. A diacrylate of claim 1, in which Y represents a member selected from the group consisting of a $C_6$–$C_{13}$ alkylene and a cyclo-alkene group.

3. A diacrylate of claim 1, in which Y is a trimethyl methylene cyclo-hexylene group.

4. A diacrylate of claim 1, in which Y represents a member selected from the group consisting of a $C_2$–$C_4$ alkylene group, 2-hydroxy trimethylene and an oxydiethylene group.

5. A diacrylate of claim 1, in which Z represents a member selected from the group consisting of a hexose residue and a hexitol residue.

6. A diacrylate of claim 5, in which Z is a member selected from the group consisting of a glucose residue and a fructose residue.

7. A diacrylate of claim 1, in which m is an integer with an average value of 2 to 2.2.

8. The diacrylate of claim 1, in which X is a direct bond.

9. The diacrylate of claim 1, in which X is oxygen and Y is ethylene.

10. A method for the preparation of a diacrylate of claim 1, in which an aliphatic isocyanate having the formula $H_2C=C(R)$—CO—X—Y—NCO is reacted with a mono- or disaccharide having the formula $Z(OH)_2$.

11. A method of claim 10, in which the reaction is carried out in a polar, aprotic solvent.

12. A method of claim 10, in which the reaction is carried out in a liquid monomer.

13. A method of claim 10, in which an aliphatic isocyanate with the formulae $H_2C=C(R)$—CO—X—Y—NCO is is reacted with a mono- or disaccharide having the formula $Z(OH)_2$, wherein Z is a glucose or fructose residue.

14. A diacrylate having the following formula:

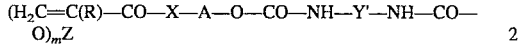                                     2 in which: A represents a member selected from the group consisting of a $C_1$–$C_8$ alkylene group, and a $C_1$–$C_8$ alkylene group substituted with a member selected from the group consisting of at least one hydroxyl and one to three ether moieties; Y' represents a member selected from the group consisting of aliphatic and cycloaliphatic groups of 2 to 22 carbon atoms, and aliphatic and cycloaliphatic groups of 2 to 22 carbon atoms having at least one ether group; m is an integer with an average value between 1.9 and 3, R is hydrogen or a lower alkyl of 1 to 4 carbon atoms, X is a direct bond, an oxygen atom or an imino group and Z is a mono- or disaccharide residue.

15. A diacrylate of claim 14, prepared by the reaction of a compound of the formula $H_2C=C(R)$—CO—X—A—OH with an aliphatic diisocyanate and a member selected from the group consisting of monosaccharides and disaccharides.

16. A method for the preparation of a diacrylate of claim 14, in which a diisocyanate with the formula, OCN—Y'—NCO, is reacted with a member selected from the group consisting of monosaccharides and disaccharides with the formulae $Z(OH)_2$, and the resulting diisocyanate with the formula, $(OCN-Y'NH-CO-O)_2Z$, is reacted with a hydroxyalkyl acrylate with the formula, $H_2C=C(R)$—CO—X—A—OH, in which A, R, X, Y' and Z are as described as in claim 14.

17. A biodegradable polymer obtained by the polymerization of a diacrylate of claim 1.

18. A biodegradable adhesive which contains a polymer of claim 17.

19. A biodegradable polymer obtained by the polymerization of a diacrylate of claim 14.

20. A biodegradable adhesive which contains a polymer of claim 19.

* * * * *